United States Patent
Ruppert

[11] Patent Number: 6,053,930
[45] Date of Patent: Apr. 25, 2000

[54] SINGLE USE LANCET ASSEMBLY

[76] Inventor: Norbert Ruppert, 1501 Lexington Ave., Deland, Fla. 32724

[21] Appl. No.: 09/075,743

[22] Filed: May 11, 1998

[51] Int. Cl.[7] .................................................. A61B 17/00
[52] U.S. Cl. ............................................................ 606/181
[58] Field of Search ..................................... 606/181–183, 606/167, 184–185; 600/564, 567

[56]  References Cited

U.S. PATENT DOCUMENTS

| | | |
|---|---|---|
| 3,030,959 | 4/1962 | Grunert ................................ 606/181 X |
| 4,388,925 | 6/1983 | Burns . |
| 4,527,561 | 7/1985 | Burns . |
| 4,616,649 | 10/1986 | Burns . |
| 4,624,253 | 11/1986 | Burns . |
| 5,152,775 | 10/1992 | Ruppert . |
| 5,487,748 | 1/1996 | Marshall et al. . |
| 5,554,166 | 9/1996 | Lange et al. ............................. 606/182 |
| 5,871,494 | 2/1999 | Simons et al. ........................... 606/181 |

*Primary Examiner*—Michael Buiz
*Assistant Examiner*—Vikki Trinh
*Attorney, Agent, or Firm*—James H. Beusse; Holland & Knight LLP

[57]  ABSTRACT

A single use lancet assembly comprises a housing for holding a manual operable lancet. A cap is slidably positioned on one end of the housing and has a projection for engaging an end of the lancet for driving a needle end of the lancet out of the housing when the cap is depressed. A plastic closure is attached to another end of the housing and has an aperture for passage of the needle. A spring member is integrally molded to the plastic closure for biasing the lancet into the housing. The cap projection and lancet end are constructed so that the projection slips over the lancet and when the lancet engages the closure so as to preclude re-use of the assembly.

14 Claims, 2 Drawing Sheets

SINGLE USE LANCET ASSEMBLY

BACKGROUND OF THE INVENTION

The present invention relates to disposable lancet assemblies and in particular to a single-use assembly for pricking a person's finger for a blood sample.

Various types of disposable lancet assemblies are known in the art, ranging from auto-loading, multiple lancet units such as that shown in U.S. Pat. No. 5,152,775 to single-use, disposable units such as that shown in U.S. Pat. No. 5,487,748. All of the recently developed types of assemblies have the common goal of providing a sterile lancet that can only be used one time. The preferred embodiment is a single-use, disposable assembly which minimizes the possibility of contamination. For such disposable assemblies, it is desirable to provide a simple, inexpensive but reliable unit.

In order to attain the goals of simplicity and low cost, it is desirable to minimize the number of components in an assembly so as to reduce labor costs. Further cost reduction can be attained by elimination of metal components, such as coil springs, and by design of the assembly such that appendages, slots and flanges are molded in situ.

SUMMARY OF THE INVENTION

Among the several objects of the present invention may be noted the provision of a single-use lancet assembly comprising plastic moldable elements and the provision of a single-use lancet assembly comprising moldable elements that are easily assembled. These objects and advantages, as well as others, will be in part pointed out and in part apparent from the description to follow. In an illustrative embodiment, the invention is shown as a single-use lancet assembly comprising a tubular body having a top end with a top opening and a bottom end with a bottom opening. A lancet is disposed in the tubular body, the lancet having an upper end and a lower end. An encapsulating member is removably attached to the lower end and encases a needle tip protruding from the lancet. A bottom flange circumscribes the lancet adjacent the lower end and an upper flange circumscribes the lancet adjacent the upper end. A closure is attached to the bottom opening of the body and has a central aperture passing therethrough for passage of the encapsulating member and needle tip. A plastic spring is integrally molded with the closure so as to be positioned between the closure and the bottom flange of the lancet for urging the lancet away from the closure. A cap is slidably fitted over the top end of the body. The cap includes at least one projection extending from an inner surface thereof for engaging the upper flange of the lancet for driving the lancet axially within the body until axial movement is opposed by a predetermined force. The projection is deflectable from the upper flange when movement of the lancet is resisted by the predetermined force. The spring is effective to retract the lancet needle tip into the body when the projection is deflected form the upper end of the lancet. The lancet assembly includes at least one guide in the body for preventing rotation of the lancet with respect to the body. Preferably, the guide comprises an axial ridge formed on an inner surface of the body which mates with a slot formed in the lancet. The slot is desirably molded in a pair of axially spaced, radially extending flanges between the upper flange and the bottom flange. It is also desirable to form the bottom flange with a larger diameter than the radially extending flanges and to mold the body with a lower portion having an inner diameter sized to fit the bottom flange. The upper portion of the body is sized to fit the smaller diameter radially extending flanges whereby the lancet cannot be withdrawn from the body through the top end.

The lancet body includes an upper portion adjacent the top end having a reduced outer diameter for receiving the cap and a radially outward extending flange circumscribing the top end for engaging a radially inward extending flange circumscribing an open end of the cap for inhibiting removal of the cap from the body. The axial range of movement of the cap is determined by the cap axial length and the length of the upper portion. The lower portion of the body has an axial extent which restricts movement of the lancet toward the cap to a distance sufficient to preclude the cap projection from withdrawing from the lancet prior to axial movement of the cap being inhibited by the flange around the top end of the body thus preventing re-use of the lancet assembly. It will be noted that each of the body, the lancet, the cap, and the closure (with integrally molded springs) are separately injection molded of a plastic resin and readily assembled into a single-use lancet.

BRIEF DESCRIPTION OF THE DRAWINGS

For a better understanding of the present invention, reference may be had to the following detailed description taken in conjunction with the accompanying drawings in which.

DETAILED DESCRIPTION OF THE INVENTION

Figure 1:
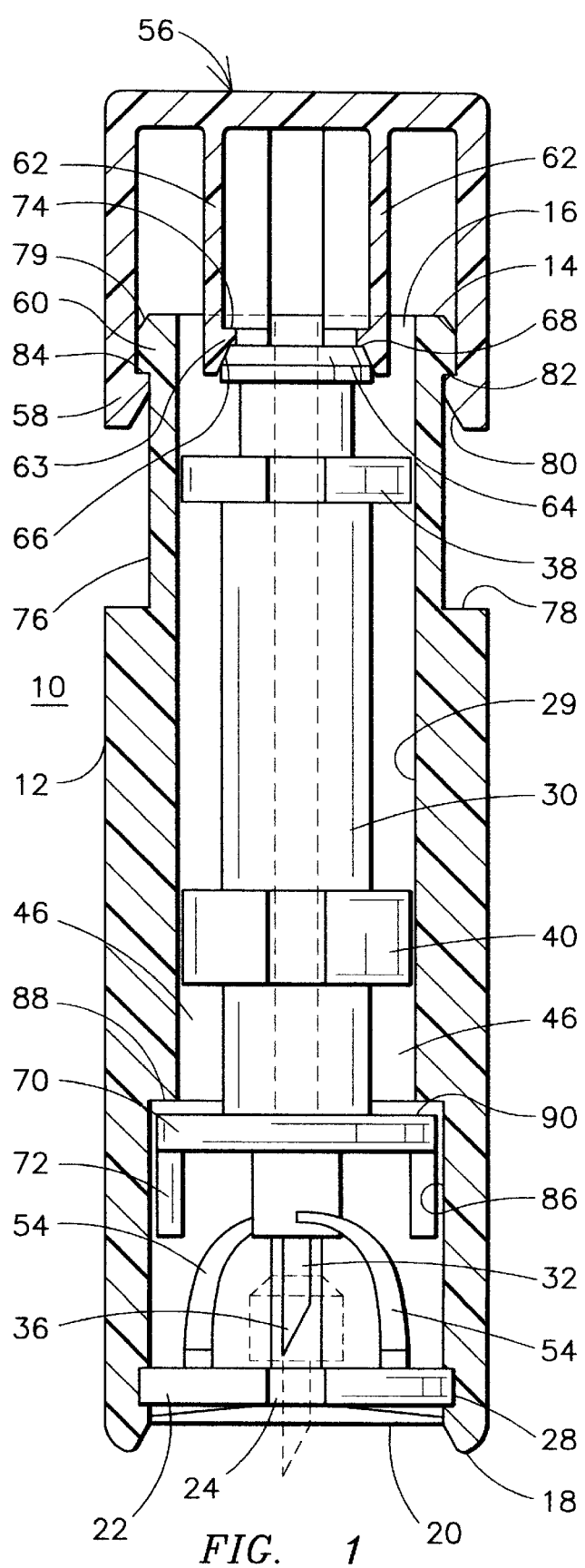
FIG. 1 is a cross-sectional view of one embodiment of the present invention.

FIG. 1 is a cross-sectional view of a single-use, disposable lancet assembly 10 illustrating one embodiment of the present invention which reduces the number of components of the assembly to reduce its manufacturing and assembling costs. The assembly 10 includes a molded, plastic, tubular body 12 having a top end 14 with a top opening 16 and a bottom end 18 with a bottom opening 20. A molded, plastic closure 22 is fitted into end 18 and has a central aperture 24 and a slot 26 extending from the edge of the closure to the aperture 24 (see FIG. 2). The closure 22 snaps into a slot 28 formed in an inner surface 29 of body 12 with the slot 28 and closure 22 being sized to create a binding fit with closure 22 to retain it in the assembled position.

Figure 3:
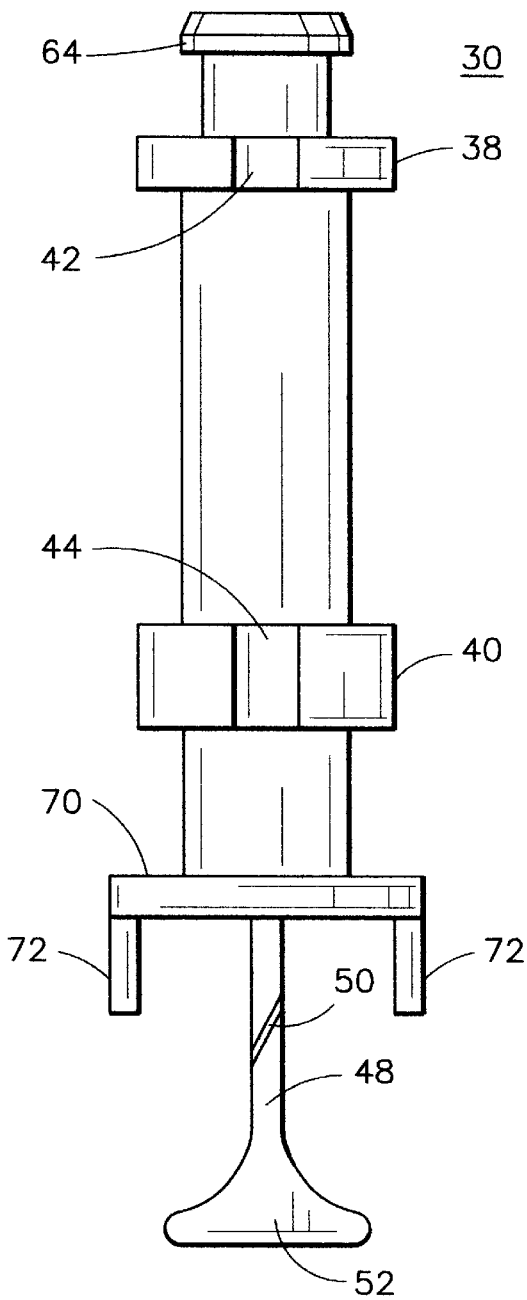
FIG. 3 is an elevation view of a lancet for use in the embodiment of FIG. 1.
Figure 4:
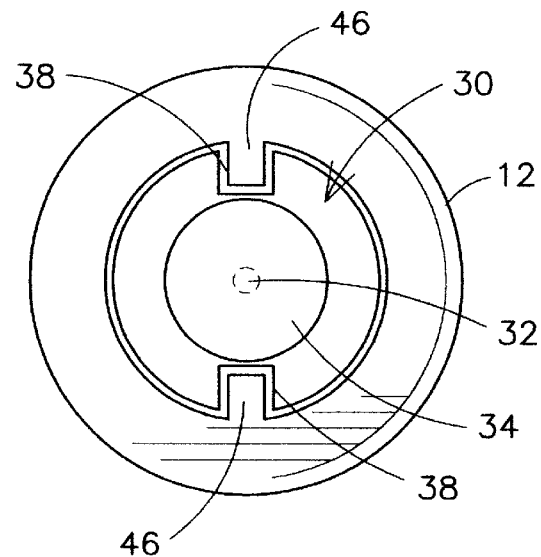
FIG. 4 is a top plan view of the embodiment shown in FIG. 1 with the upper cup removed.

A lancet 30, shown in FIGS. 3 and 4, fits into body 12. The lancet 30 comprises a metal needle 32 molded in situ in a solid plastic housing 34. One end 36 of the needle 32 is formed with a sharpened point. The housing 34 is designed to fit into body 12 and has a pair of equal diameter, spaced flanges 38 and 40 which guide the lancet 30 within the body 12 of the lancet assembly. Each of the flanges 38 and 40 are formed with slots 42 and 44, respectively, on opposite sides thereof, which fit in sliding engagement with axially extending guides or runners 46 integrally formed on the inner surface 29 of body 12. While the lancet 30 could be guided for axial movement within body 12 by the outer circumferential face of each of the flanges 38, 40, the runners 46 are desirable to prevent the lancet from being rotatable within body 12.

The needle pointed end 36 is protected by a removable plastic element 48 (FIG. 3) which is separatable from lancet 30 along a weakened, thin joint 50. When installed in the lancet assembly, the point is exposed by grasping the widened tab portion 52 of element 48 and twisting while pulling to remove element 48. It is during this process of removing the element 48 that the runners 46 come into play to prevent lancet 30 from rotating within body 12. The body 12 is sized to provide a minimum sliding spacing between the upper and lower flanges 38, 40, respectively, of lancet 30 and the inner surface 29 of body 12.

When the lancet 30 is assembled into the lancet assembly, the lancet 30 is biased away from end closure 22 by spring elements 54 which are preferably integrally molded as part of plastic closure 22.

Figure 2:
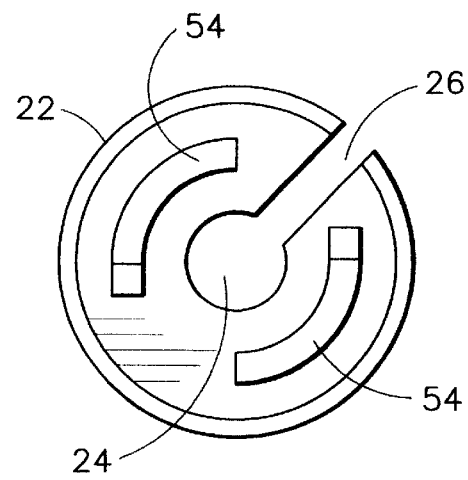
FIGS. 2 and 2A are top plan view and elevation view, respectively, of an integral closure/spring member for use in the embodiment of FIG. 1.
Figure 2A:
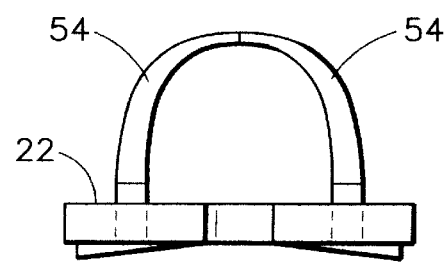

FIG. 2 shows the spring elements 54 in an end view while FIG. 2A shows the elements 54 in an elevation view. The elements 54 are raised, cantilevered plastic members having sufficient "memory" or resiliency to push the lightweight lancet 30 away from closure 22. The purpose of the spring elements is to effect retraction of the lancet 30 after a single use.

Figure 5:
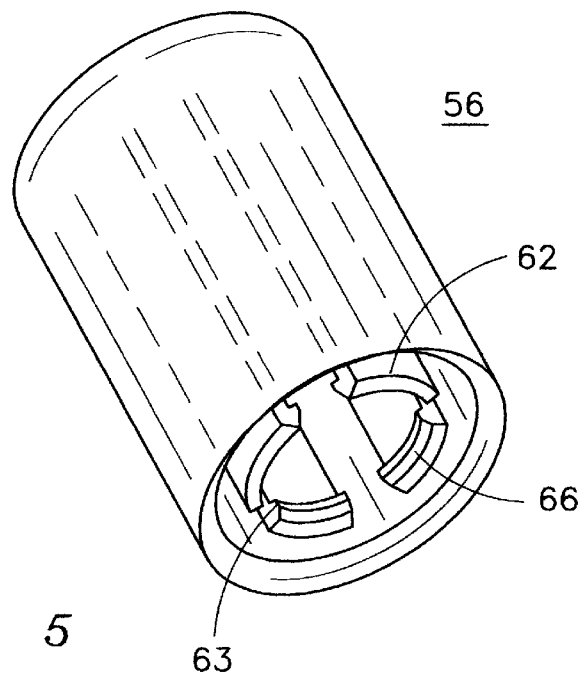
FIG. 5 is a perspective view of the cap shown in FIG. 1.

With the lancet 30 assembled into assembly 10, the lancet 30 can be driven to expose needle point 36 by compressing lancet 30 against spring elements 54. The driving device is a cap 56 which snaps onto end 14 of body 12. The cap 56 is held in place by a circumferential flange 60 formed about end 14 of body 12 which cooperates with an inner annular flange 58 circumscribing cap 56 adjacent its open end. Considering the perspective view of cap 56 in FIG. 5 in conjunction with FIG. 1, the cap has a plurality, preferably four, of internal elongated, flexible engagement members 62 for engaging an upper flange 64 on lancet 30. The members 62 are each integrally molded with cap 56 and attached to an inner surface of the top flat portion of cap 56. The distal end of each member 62 incorporates a projection 63 which is adapted for contacting the flange 64 against an angular face 66 and a narrow ledge 68. More particularly, the members 62 are spaced such that the four members contact the flange 64 about a periphery thereof and the resiliency of the members 62 hold the faces 66 against the flange 64 such that the flange 64 is engaged with the ledge 68. This arrangement allows the cap 56 to be pressed toward lancet 30 whereby lancet 30 can be advanced or driven toward closure 22. However, when a lower footed flange 70 on lancet 30 contacts closure 22 via the extending foot elements 72, the members 62 will slip over the flange 64, i.e., the sloped faces 66 will cause the members 62 to spread apart and slide past the flange 64. Once the members 62 pass over flange 64, the members 62 spring back to their normal position. At this point, the spring members 54 are effective to push lancet 30 toward end 14 thereby retracting needle point 36. The inner surface 74 of ledge 68, which is relatively wide, can engage an underside of flange 64 allowing the lancet to be pulled back into the assembly by the cap 56. However, the range of movement of cap 56 is limited, as described below, so that the cap cannot be withdrawn far enough to allow the engagement members 62 to pass over the flange 64 in a reverse direction. This limited movement prevents the lancet assembly from being re-used.

The range of motion of cap 56 is determined by the axial length of a reduced diameter portion 76 of lancet assembly body 12. As shown in FIG. 1, the portion 76 is adjacent top end 14 of body 12 opposite closure 22 and is defined by a circumferential shoulder 78 and the circumferential flange 60. The internal diameter of flange 58 of cap 56 is adapted and sized to slidingly fit on the portion 76 and to abut the shoulder 78 when the cap is fully pressed onto body 12. The cap 56 is retained on body 12 by the inner annular flange 58 circumscribing the cap at its open end which flange 58 engages outer circumferential flange 60 about end 14 of body 12. Both the outer upper edge 79 of flange 60 and the inner lower edge 80 of flange 58 are chamfered to facilitate assembly of the cap 56 onto body 12. However, the lower edge 82 of flange 60 and the inner edge 84 of flange 58 are formed in planes normal to the axis of the body 12 to deter removal of the cap 56 once installed on the body 12.

It can be seen that the lower end of body 12 adjacent end 18 is formed with a portion 86 which has a slightly larger inner diameter as compared to an inner diameter of the body 12 over the portion occupied by the runners 46. This enlarged diameter portion 86, in conjunction with closure 22, determines the range of axial movement of lancet 30 within body 12. More particularly, an inner shoulder 88 defining the transition between portion 86 and the smaller diameter passage through body 12 functions as an inner stop by engaging an abutting surface 90 of flange 70 of lancet 30. This stop limits the movement of lancet 30 towards cap 56 and prevents removal of the lancet from body 12. Movement away from cap 56 is limited by engagement of elements 72 against an inner surface of closure 22. The axial length of portion 86, i.e., the position of shoulder 88, is important since it must allow the lancet 30 to be retracted sufficiently far to prevent the engagement members 62 from being pulled over the flange 64 of lancet 30 before the axial movement of the cap 56 is stopped by shoulder 82.

It will be apparent from the above description that the lancet assembly 10 is produced from a minimal number of individual components, each of which is designed to be produced by injection molding using relatively inexpensive molds. The assembly of the device begins by inserting the lancet 30 into body 12 from the end 20. The closure 22 is then snapped into place by passing slot 26 about element 48. The cap 56 is then pressed on end 14 of body 12 to complete the assembly.

To use the lancet assembly 10, the end 52 of element 48 is grasped while holding the body 12 and pulling and twisting the element 48 to separate element 48 along joint 50. The spring elements 54 react against lancet 30 and hold the needlepoint 36 retracted within the holder body 12 once the element 48 is removed. The assembly 10 is then ready for use and such use is achieved by pressing the closure 22, which has a concave shaped outer surface, onto a person's finger and then pushing the cap 56 downward. The members 62 will engage upper flange 64 and drive the needle outward of closure 22 to puncture the finger. When the footed elements 72 contact the inner surface of closure 22, the movement of lancet 30 will be stopped and the members 62 will slide over flange 64 and preclude any further driving force being applied to lancet 30. The spring elements 54 can then force retraction of the needle into body 12. As discussed above, the lancet assembly 10 cannot be re-used since the cap 56 cannot be retracted far enough to allow the members 62 to pass back over the flange 64. While the invention has been described in what is presently considered to be a preferred embodiment, many variations and modifications will become apparent to those skilled in the art. Accordingly, it is intended that the invention not be limited to the specific illustrative embodiment but be interpreted within the full spirit and scope of the appended claims.

What is claimed is:

1. A single-use lancet assembly comprising:

a tubular body having a top end with a top opening and a bottom end with a bottom opening;

a lancet disposed in said tubular body, said lancet having an upper end and a lower end, an encapsulating member removably attached to said lower end and encasing a needle tip protruding from said lancet, a bottom flange circumscribing said lancet adjacent said lower end, and an upper flange circumscribing said lancet adjacent said upper end;

a closure attached to said bottom opening of said body and having a central aperture passing therethrough for passage of said encapsulating member;

spring means positioned between said closure and said bottom flange of said lance for urging said lancet away from said closure; and a cap slidably fitting over said top end of said body, said cap including engagement means extending from an inner surface thereof for engaging said upper flange of said lancet for driving said lancet axially within said body until axial movement is opposed by a predetermined force, said engagement means being deflectable from said upper flange when movement of said lancet is resisted by a said predetermined force, said spring means being effective to retract said lancet needle tip into said body when said engagement means is deflected from said upper end of said lancet.

2. The lancet assembly of claim 1 and including means in said body for preventing rotation of said lancet with respect to said body.

3. The lancet assembly of claim 2 wherein said means in said body for preventing rotation comprises at least one guide formed on an inner surface of said body and extending axially therealong and a mating slot formed in said lancet for receiving said guide.

4. The lancet assembly of claim 3 wherein said lancet includes a pair of axially spaced, radially extending flanges between said upper flange and said bottom flange, said mating slot being formed in each of said radially extending flanges.

5. The lancet assembly of claim 4 wherein said bottom flange has a larger diameter than said radially extending flanges and said body includes a lower portion having an inner diameter sized to fit said bottom flange and an upper portion sized to fit said radially extending flanges whereby said lancet cannot be withdrawn from said body through said top end.

6. The lancet assembly of claim 5 wherein said body includes an upper portion adjacent said top end having a reduced outer diameter for receiving said cap, a radially outward extending flange circumscribing said top end for engaging a radially inward extending flange circumscribing an open end of said cap for inhibiting removal of said cap from said body.

7. The lancet assembly of claim 6 wherein said lower portion has an axial extent which allows said lancet to move toward said cap a distance sufficient to preclude said engagement means from withdrawing from said lancet prior to axial movement of said cap being inhibited by said flange around said top end of said body.

8. The lancet assembly of claim 1 wherein said spring means comprises at least one integrally formed, cantilevered plastic member extending from a surface of said closure.

9. The lancet assembly of claim 8 wherein said bottom flange includes at least one axially extending foot for contacting said closure whereby said spring member is only partially compressed between said lancet and said closure.

10. The lancet assembly of claim 9 wherein each of said body, said lancet, said cap, and said closure are separately injection molded of a plastic resin.

11. A single use lancet assembly comprising:

a housing having an axial passageway therethrough;

a lancet including a needle molded in situ in a plastic shell, said lancet being adapted and sized for fitting in said passageway in said housing;

a cap slidably positioned on a first end of said housing and having at least one internal projection for engaging a first end of said lancet;

a plastic closure attached to another end of said housing and having an aperture for passing an end of said needle when said lancet is advanced toward said closure by movement of said cap; and raised, cantilevered plastic spring members integrally molded with said plastic closure for resisting movement of said lancet toward said closure.

12. The lancet assembly of claim 11 and including a flange circumscribing said first end of said lancet for engaging said at least one projection, said flange and said projection being configured to allow said projection to slip over said flange when movement of said lancet is opposed by a predetermined force.

13. The lancet assembly of claim 11 wherein said spring means comprises at least one plastic projection extending from said closure and having a generally arcuate shape.

14. The lancet assembly of claim 13 and including means for guiding said lancet within said housing for axial movement while inhibiting rotational movement.

* * * * *